United States Patent
Wang et al.

(10) Patent No.: US 7,732,575 B2
(45) Date of Patent: Jun. 8, 2010

(54) MICROPARTICLES WITH ENHANCED COVALENT BINDING CAPACITY AND THEIR USES

(75) Inventors: Xinwen Wang, Bedford, MA (US); Sukanta Banerjee, Pennington, NJ (US)

(73) Assignee: Bioarray Solutions, Ltd., Warren, NJ (US)

( * ) Notice: Subject to any disclaimer, the term of this patent is extended or adjusted under 35 U.S.C. 154(b) by 405 days.

(21) Appl. No.: 11/695,686

(22) Filed: Apr. 3, 2007

(65) Prior Publication Data

US 2008/0247905 A1 Oct. 9, 2008

Related U.S. Application Data

(63) Continuation of application No. 10/947,095, filed on Sep. 22, 2004, now Pat. No. 7,595,279.

(60) Provisional application No. 60/504,716, filed on Sep. 22, 2003.

(51) Int. Cl.
*C07K 17/00* (2006.01)
*C07H 21/04* (2006.01)
*C12Q 1/68* (2006.01)

(52) U.S. Cl. .......................... 530/363; 536/23.1; 514/2; 435/6

(58) Field of Classification Search ....................... None
See application file for complete search history.

(56) References Cited

U.S. PATENT DOCUMENTS

2002/0155481 A1  10/2002  Hirota et al.

OTHER PUBLICATIONS

Olejnik et al, "Photocleavable biotin phosphoramidite for 5'-end-labeling, purification & phosphoryiation of oligonucleotides",Nucleic Acids Research 1996, vol. 24, 2:361-366.

Boyd et al., "Tosyl Chloride activation of a rayon /polyester cloth for protein immobilization", Biotechnology Techniques, Apr. 1993, vol. 7, 4:277-282.

*Primary Examiner*—Anand U Desai
(74) *Attorney, Agent, or Firm*—Womble Carlyle Sandridge & Rice, PLLC

(57) ABSTRACT

Disclosed are proteins which are covalently bound to a solid support at a first temperature where they have a first configuration, and then biomolecules are attached to the bound proteins at a higher temperature at which the proteins have more exposed functional groups, each such group being capable of covalently bonding to a biomolecule. The biomolecule can be, for example, a nucleic acid, including an amine functionalized oligonucleotide. The proteins can include, BSA (Bovine Serum Albumin) which can be bound using a reaction with the surface of a tosyl-activated microparticle.

7 Claims, 8 Drawing Sheets

MICROPARTICLES WITH ENHANCED COVALENT BINDING CAPACITY AND THEIR USES

RELATED APPLICATIONS

This application is a continuation of U.S. application Ser. No. 10/947,095, filed Sep. 22, 2004, now U.S. Pat. No. 7,595,279, which claims priority to U.S. Provisional Application No. 60/504,716, filed on Sep. 22, 2003.

FIELD OF THE INVENTION

This invention is in the field of polyelectrolyte chemistry.

BACKGROUND

As an alternative to solve many of the problems associated with diagnostic use of "spotted arrays" of oligonucleotides (the problems are outlined in "Multianalyte Molecular Analysis Using Application-Specific Random Particle Arrays," U.S. application Ser. No. 10/204,799, filed on Aug. 23, 2002; WO 01/98765) preferred arrays are formed by binding oligonucleotide probes to encoded microbead particles, including, encoded particles made of polymer resin. See U.S. patent application Ser. No. 10/271,602 "Multiplexed Analysis of Polymorphic Loci by Concurrent Interrogation and Enzyme-Mediated Detection," filed Oct. 15, 2002, and Ser. No, 10/204,799 supra. The encoded particle-probe conjugates are then assembled in a 2D array format and placed in contact with samples anticipated to contain target polynucleotides with subsequences complementary to the probes, where the target polynucleotides in the samples were previously fluorescently labeled. Binding between the probes and targets is determined by the presence of a fluorescent assay signal. Particular probes generating a positive assay signal can be determined by decoding the array.

There are several known and commercially available methods for attachment of oligonucleotide probes to microbeads. A great number of covalent immobilization schemes for oligonucleotide probes to microparticles have been devised and are available either in open literature or commercially. Traditional covalent immobilization techniques use functionalized beads (i.e, beads functionalized with reactive groups like amino, carboxyl, tosyl, aldehyde, epoxy, hydrazide and others) to link to complementary functional groups on the end of oligonucleotide probes (Maire K. Walsh, Xinwen Wang and Bart C. Weimer, Optimizing the immobilization of single-stranded DNA onto glass beads, J. Biochem. Biophys. Methods 2001; 47:221-231). Often times such binding protocols lead to improper orientation and steric hindrance problems. The hybridization performance of such covalently immobilized probes can be improved by introduction of spacer molecules (Edwin Southern, Kalim Mir and Mikhail Shchepinov; Molecular Interactions on Microarrays, Nature Genetics Supplement, 21, 1999, pp. 5-9), however, implementation is often difficult and impractical.

A practical and robust probe binding chemistry is therefore important for the optimal performance of a microbead array based assay. The chemistry must allow the probes to bind to the particles with high efficiency, in order to maintain a consistent concentration of probes on the bead surface and also the reaction must not alter the efficiency of probe-target binding. Moreover, the reaction must have minimum batch to batch variability. In one commonly used method, functionalized microparticles are coated with Neutravidin (Pierce, Rockford, Ill.), streptavidin or avidin, which are biotin binding proteins, to mediate immobilization of biotinylated probes. The avidin-biotin interaction is highly specific and one of the strongest known (with an association constant ($K_A$) of the order of $10^{15}$ $M^{-1}$ in aqueous solutions) and provides nearly irreversible linkage between the bead surface immobilized protein and the biotinylated probe molecule. See U.S. patent application Ser. No. 10/271,602, supra. The method described below for binding probes to polyelectrolytes are preferred to these known methods, because they were demonstrated as capable of inducing attachment of greater numbers of oligonucleotides to beads.

SUMMARY

A polyelectrolyte having multiple exposed functional groups, each such group being capable of covalently bonding to a molecule, is immobilized on a surface for the purpose of bonding to a biomolecule. The biomolecule can be, for example, a nucleic acid, e.g., an amine functionalized oligonucleotide. The polyelectrolyte can include, e.g., BSA (Bovine Serum Albumin) which is bound to a functionalized surface using a covalent immobilization strategy, e.g., reaction with the surface of a tosyl-activated microparticle. Following such reaction, exposed reactive functional groups on the protein, such as amine, carboxyl, thiol, hydroxyl groups can further be utilized to covalently couple the oligonucleotide of interest using suitable chemistry.

In one embodiment oligonucleotides modified at a terminal position (the 3' or 5' terminal position) with amines (e.g., amino modified oligonucleotides) are covalently bound to BSA using an EDAC (1-ethyl-3-(3-dimethylaminopropyl) carbodiimide) reaction (see, e.g., D. Seligal et al., Analytical Biochemistry 218:87091 (1994)). The covalent reaction results in the formation of an amide bond between the amine group at the terminus of the oligonucleotide and carboxyl groups on the BSA. The reaction is illustrated in FIG. 1.

The functionalized surface can be the surface of a bead or microparticle, which can be composed of any of a number of materials, including polymers, polymer resins, glass, latex or others which can be functionalized for immobilization of a polyelectrolyte. Experiments were performed comparing BSA-coated beads with human serum albumin ("HSA") another exemplary polyelectrolyte, and with Neutravidin as well. The results of hybridization experiments indicated that the BSA-coated beads were capable of attaching greater concentrations of oligonucleotides to the beads.

DETAILED DESCRIPTION

Example 1

Preparation of BSA-Coated Tosyl Functionalized Beads

Figure 1:
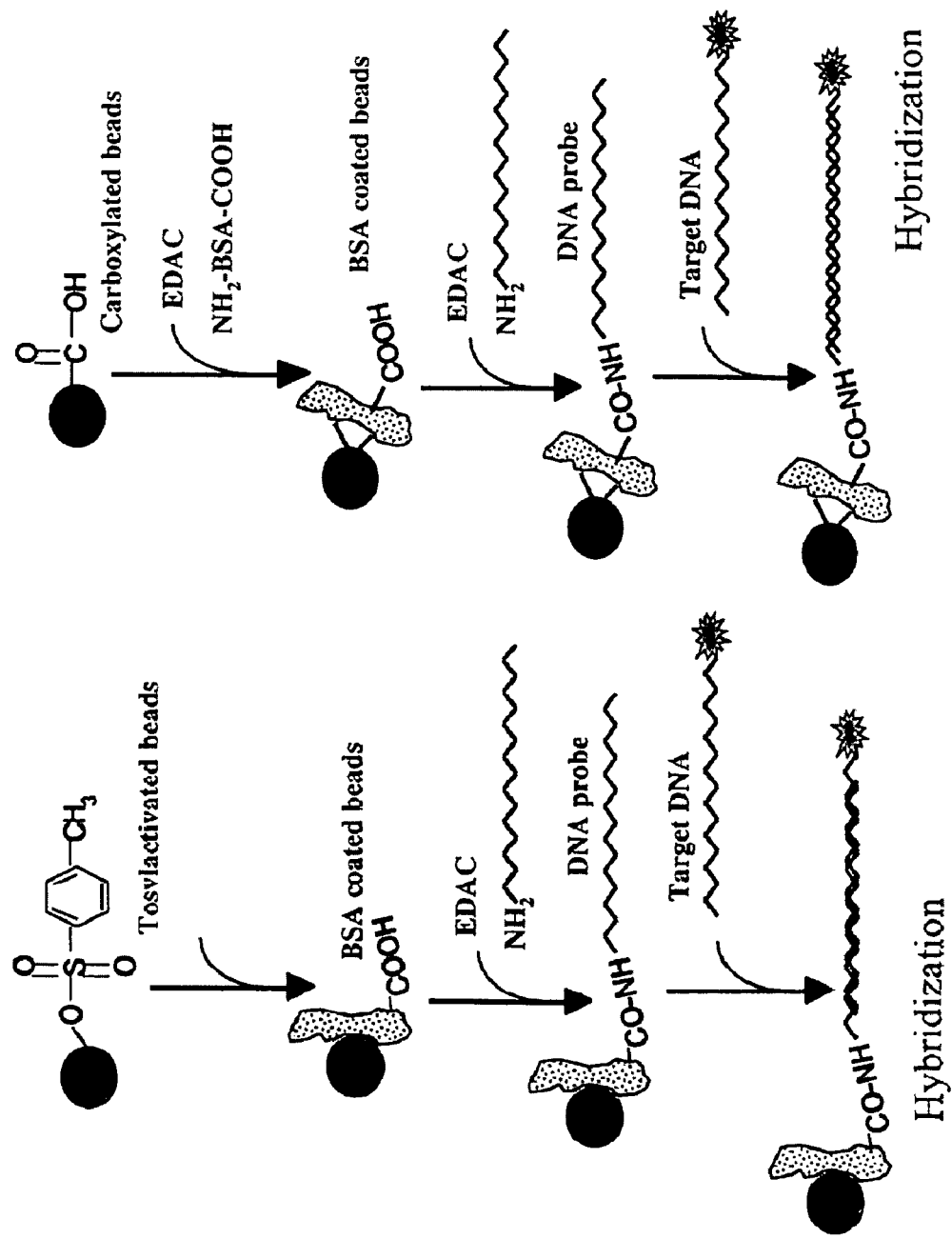
FIG. 1 illustrates the bonding of BSA to functionalized beads and the bonding of an oligonucleotide probe to the BSA using an EDAC reaction.

BSA solution at the concentration of 5 mg/mL is prepared by dissolving 50 mg of BSA in 10 mL of PBS. 2.0 mL of PBS-T is added to a 15 mL centrifuge tube. 1 mL of fluorescence colored beads at the concentration of 1% solids (10 mg) are transferred into the centrifuge tube, and mixed well by vortexing. The beads are spun down by centrifugation at 3,500 rpm for 4+/−0.5 minutes, and the supernatant is decanted. The beads are re-suspended by adding 3.0 mL of PBST into the tube, and mixed well by vortexing. The beads are again spun down by centrifugation at 3,500 rpm for 4+/−0.5 minutes, and the supernatant is discarded. 3.0 mL of BSA solution (5 mg/mL) are added to the beads, and mixed well by vortexing. The tubes are placed on a shaker in a 37° C. incubator, and the beads are allowed to react overnight with mixing at 250 rpm.

Thereafter, the beads are spun down by centrifugation at 3,500 rpm for 4 minutes, and the supernatant is discarded. The beads are then washed by adding 3.0 mL of PBS-T to the tube, and mixed on a vortex mixer. The beads are then again centrifuged at 3500 rpm for 4+/−0.5 minutes, and the supernatant is poured off. The washing and centrifuging steps are then repeated.

3.0 mL of storage buffer (0.1 M PBS containing 0.1% $NaN_3$), are added, and mixed on a vortex mixer. The beads are again centrifuged at 3,500 rpm for 4+/−0.5 minutes, and the supernatant is poured off. The beads are then resuspended in 1 ml of storage buffer by vortexing. The beads are at a concentration of 1% solids (10 mg/mL), and are stored at 4-6° C. They are ready for attachment of amine-containing biomaterials (e.g., BSA) through the EDAC reaction, as described below in Example 3.

Example 2

Preparation of BSA-Coated Carboxyl Functionalized Beads

The coupling of BSA to carboxylated particles is carried out as follows. 100 µl of carboxylated particles at a concentration of 1% solids is transferred to a 2 ml Eppendorf tube. The beads are then pelleted by centrifugation and the supernatant removed. Following this, the beads are washed 1× with 1 ml of MES (details) buffer (pH 4.5). Separately a stock solution of BSA (5 mg BSA/ml) in MES buffer and EDC (20 mg/ml) in MES buffer are prepared, 100 µl of the BSA stock solution is added to the bead pellet and the suspension mixed well by vortexing. Following this, 400 µl of the EDC stock solution is added to the bead suspension, mixed well by vortexing and allowed to react a room temperature for 1 hr with end-over-end mixing. After 1 hr incubation, 100 µl of PBS-T is added to the suspension and the beads centrifuged. The pellet is washed twice with 1 ml PBS-T by centrifugation-redispersion cycle, and the beads are finally suspended in 100 µl of storage buffer (0.1 M PBS containing 0.1% sodium azide, $NaN_3$) and stored at 4-6° C.

Example 3

EDAC Reaction for Coupling of Aminated Oligonucletide Probes to BSA Beads

The coupling of aminated oligonucletide probes to the beads, prepared as in Example 1 and 2, was carried out as follows A series of 1.5 ml Eppendorf tubes were taken and labeled to identify the type of microparticle and the oligonucletide probe to be coupled. Following this, 500 µL of PBST was dispensed into each tube, followed by 100 µL of BSA coupled beads at concentration of 1% solids. The tubes were mixed well with a vortex mixer for 10 seconds. The beads were then spun down at 9500 rpm for 2+/−0.5 nm, and the supernatant discarded. A 500 µL aliquot of 0.05 M MES buffer (pH4.5) was added to the pellet, and mixed well by vortexing. The beads were then centrifuged at 9500 rpm for 2+/−0.5 minutes, and the supernatant discarded. A 500 ul aliquot of 0.05 M of EDAC in MES buffer (prepared right before use) was added to the beads, and mixed well by vortexing. Following 10 µL each of amino modified DNA probes (e.g., probe MS-508 N25, purchased from Integrated DNA Technologies, Inc., Coralville Iowa) was added at a concentration of 100 µM to each of the tubes containing the bead suspensions, and mixed well. The reaction is allowed to proceed for 1 hour at room temperature (20-25° C.) with end-over-end mixing.

After the incubation, 100 µL PBS-T is added to each tube, and mixed by vortexing. The beads are then spun down in a centrifuge at 9500 rpm for 2+/−0.5 minutes, and the supernatant discarded. The beads are then washed twice with 500 ul PBS-T using the centrifugation redispersion cycle.

The beads are resuspended in 100 µL of PBST to bring the final concentration to 1% solids, and stored at 4-6° C. for further use.

Figure 2:
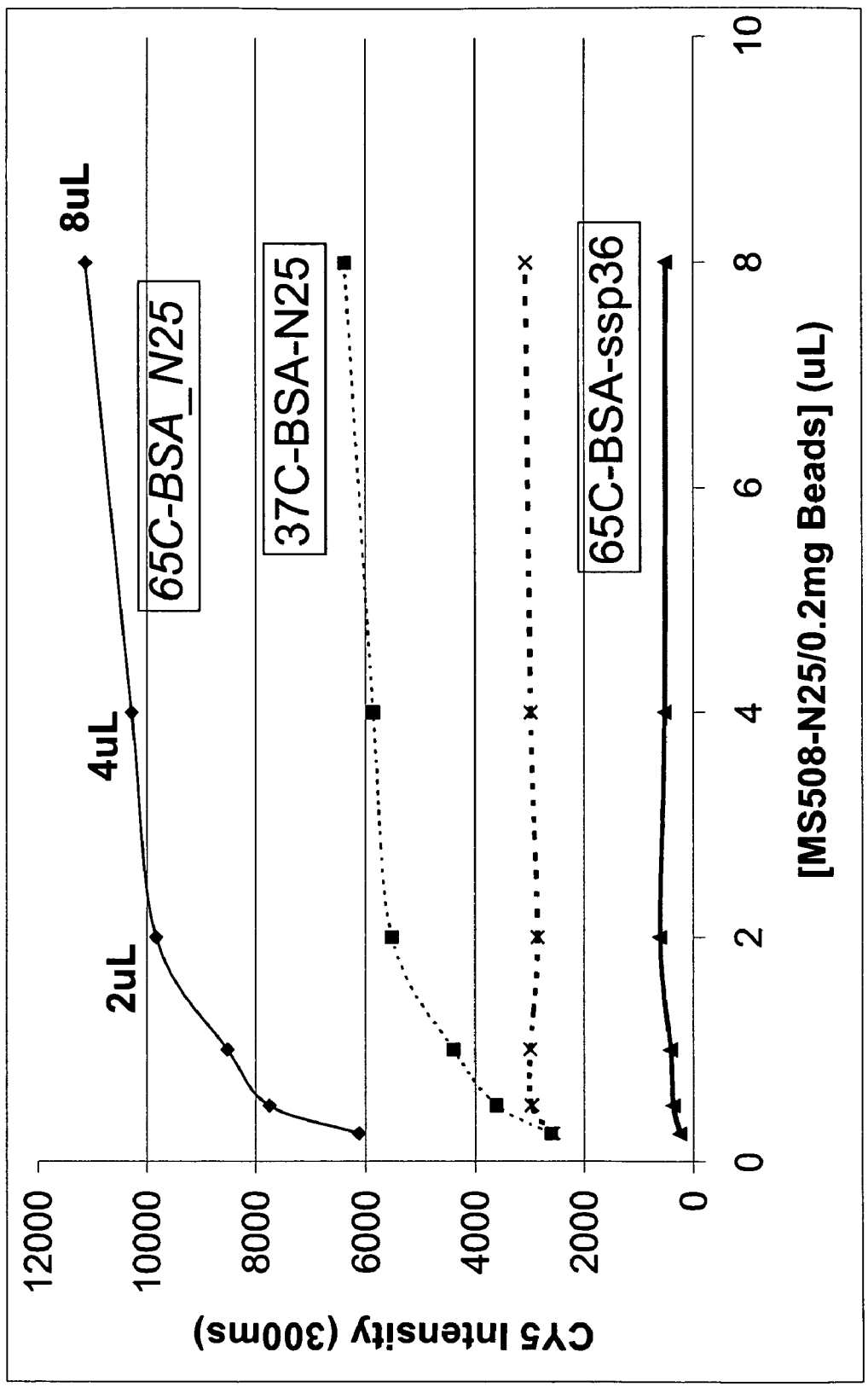
FIG. 2 shows the hybridization signals from oligo-functionalized BSA coupled beads as a function of the amount of added aminated probe for coupling. A perfectly matching probe was attached to two sets of BSA-coupled beads. BSA was coupled to the first set of beads at 65° C. and to a second set at 37° C. A much higher hybridization efficiency was noted (higher signal) on the first set of beads to which BSA was coupled at 65° C. A third set of beads coupled with BSA at 65° C. and functionalized with a mismatched negative control probe shows negligible hybridization, thus indicating that the enhanced signal is not a result of increased non-specific binding.

The hybridization performance (see Example 4 for protocol) of oligonucleotide functionalized particles as a function of added amount of oligo (0.25, 0.5, 1, 2, 4, 8 ul of 100 uM/200 ug particles) is shown in FIG. 2. The amount described above 10 ul of 10 uM/1 mg thus represents a saturation concentration. Also, the beads with BSA coupled at higher temperature show improved hybridization performance as described in detail later.

Example 4

Hybridization Assay Using Oligonucletide Functionalized Beads

1. Bead mixtures are assembled on 8 different chips. Stock fluorescently labeled DNA target solution (MS508-90mer-CY5) is prepared in hybridization buffer (1×TMAC. Eight different serial dilutions are prepared from the stock target solution. 20 μl of each of the serially diluted target solutions are then added to the eight separate chips.
2. A slide, containing the chips, is placed in a hybridization heater/shaker, and incubated at 55° C. for 20 minutes at 100 rpm.
3. The slide is removed and cooled to room temperature, and the hybridization solution is removed with the transfer pipette.
4. 20 μl of 1×TMAC is added to each chip, and the chip is washed by pipetting the solution 8 to 10 times.
5. The washing solution is removed and 5 ml of mounting solution (1×TMAC) is added to each chip, and the assay signal (CY5) is read under a fluorescent microscope using a coverslip.
6. A titration curve is plotted of the hybridization signal (CY5) vs DNA probe concentration.

Figure 3:
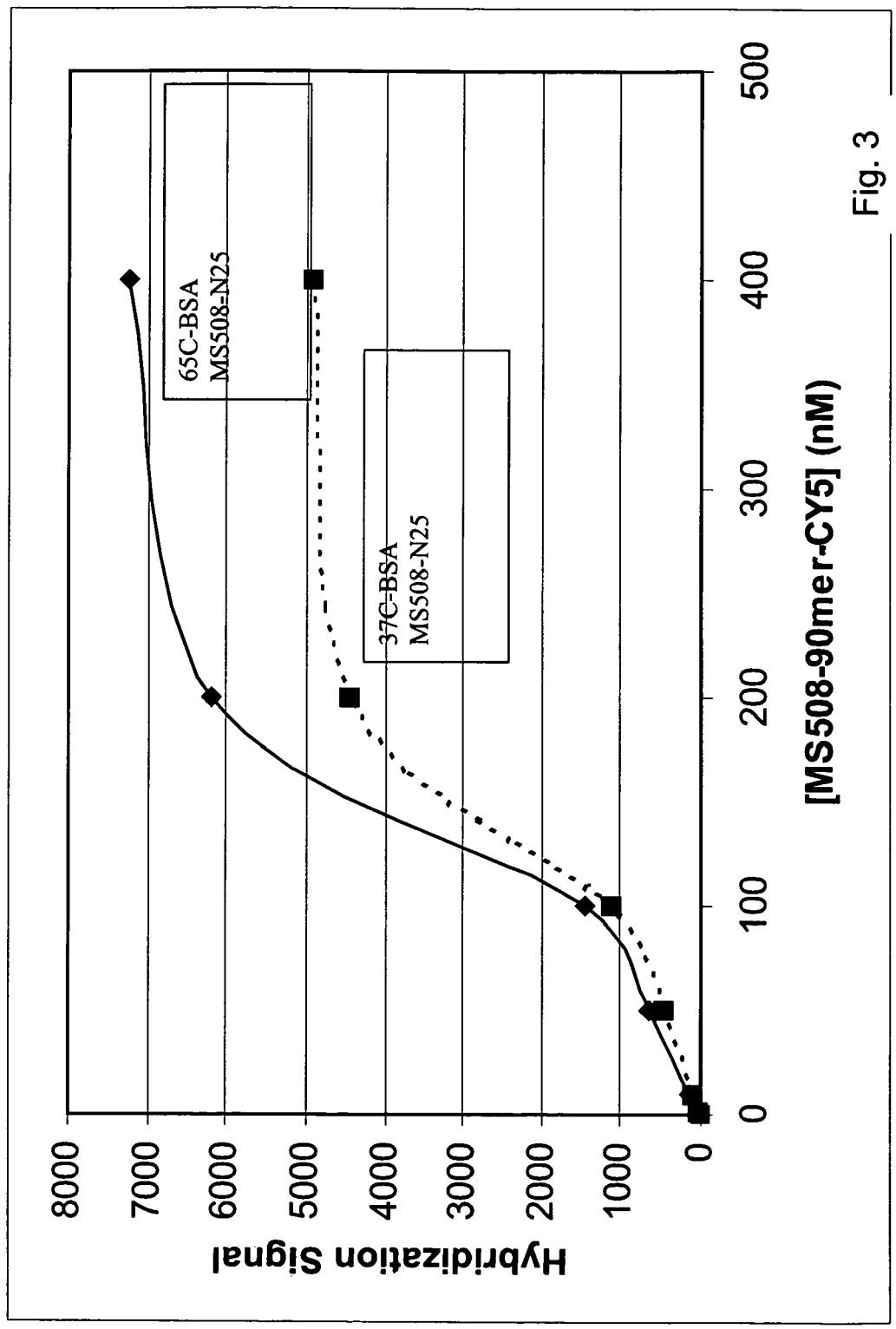
FIG. 3 shows titration results of BSA coupled beads. As in FIG. 2, efficiency of hybridization is greater for the beads coupled with BSA at a higher temperature than at a lower temperature, as demonstrated by the difference in hybridization signal from a target placed in contact with an oligonucleotide probe bound to BSA-coupled beads where BSA was coupled to one set of beads at 37° C. and where BSA was coupled to another set of beads at 65° C. (see Example 4)

Example of titration curves are shown in FIG. 3.

Example 6

Experiments were conducted to compare the effect of adding EDAC to the bead-probe suspension twice (EDAC is known to hydrolyze very quickly at acidic pH) to assess whether this leads to an enhanced binding of probes to the BSA layer. First, the probe MS-508-N25 was coupled to BSA-coated beads under each of the following condition; (10 μl 100 μM probe/100 μl 1% beads). One-half of the beads were removed from the 1× tube after one hour of reaction time, and fresh EDAC was added, and then the reaction proceeded in this tube for one additional hour. The whole process was then repeated for the non-matching probe SSP 36. Each set of beads were pooled with the non-specific beads and assembled on a chip, and then all sets were placed in contact with target MS 508-40mer-Cy5 under hybridizing conditions. Results were then recorded, and are summarized below in Table II. 2×EDAC addition provided higher hybridization signals.

TABLE II

| Probe Concentration | Model Assay Cy5 Signal | CV | Non-specific Cy5 Signal | CV |
|---|---|---|---|---|
| 1X EDAC | 536.1 | 0.17 | 79.9 | 0.26 |
| 2X extra EDAC | 732.9 | 0.17 | 53.3 | 0.19 |

Example 6

BSA Coupling to Tosyl Activated Beads at Different Temperatures and their Hybridization Characteristics 2.0 mL of PBST was added to each of five 15 mL centrifuge tubes and 1 mL of fluorescence colored beads, at the concentration of 1% solids (10 mg), was added to each tube, and then the beads were mixed by vortexing. The beads were spun down by centrifugation at 3,500 rpm for 4+/−0.5 minutes, and the supernatant was decanted. The beads were then resuspended in 3.0 mL of PBST, mixed well by vortexing, and again spun down by centrifugation at 3,500 rpm for 4+/−0.5 minutes. The supernatant was then poured off.

2 mL of PBS (pH7.2) and 1 mL of BSA solution (50 mg/mL in PBS) was added to each tube, and mixed well by vortexing. The ambient temperature in an incubator for each of the tubes was set as follows: tube A—22° C. tube B—37° C., tube—50° C., tube D—65° C. and tube E—75° C., and the beads were allowed to react with BSA for 14 hours at the designated temperature, with end-over-end mixing. The tubes were then cooled to room temperature, and the beads spun down by centrifugation at 3,500 rpm for 4 minutes, and the supernatant poured off. The beads were then washed by adding 3.0 mL of PBST to the tube mixed on a vortex mixer, and spun down at 3500 rpm for 4+/−0.5 minutes. The supernatant was poured off.

1 mL of storage buffer (PBS containing 0.1% $NaN_3$) was added, and the tubes were mixed on a vortex mixer. The bead concentration was 1% solids (10 mg/mL). The BSA coupled beads were stored at 4-6° C.

The 25-mer MS-508 N25 biotinylated oligonucleotide probe was conjugated to each set of beads through the EDAC coupling method described above. Each set of beads was then contacted with a fixed concentration of labeled target (a 90-mer oligonucleotide labeled with Cy-5) for the probe under hybridizing conditions. The quantity of label on the beads correlates with the probe concentration on the beads.

Figure 4:
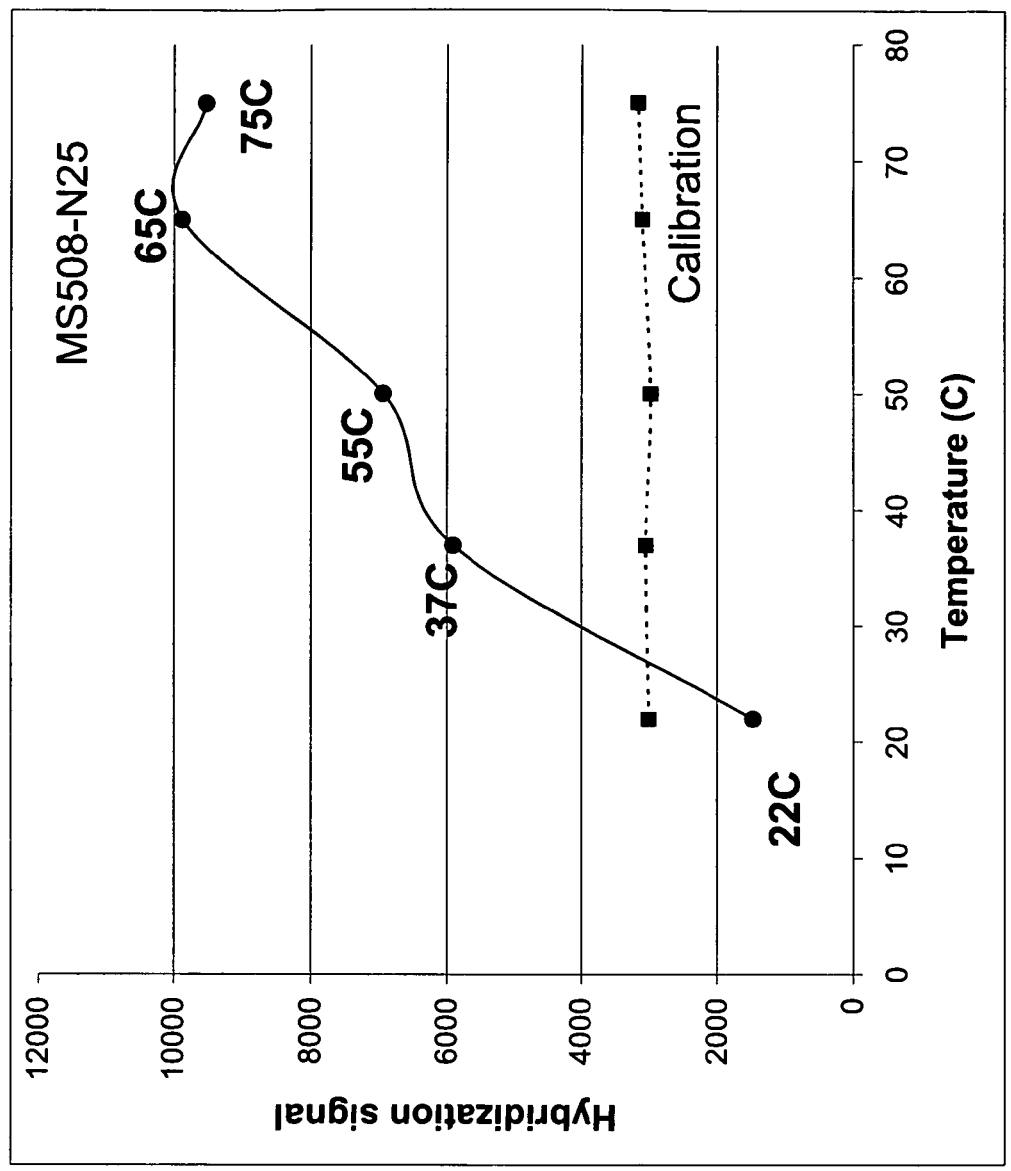
FIG. 4 indicates a differences in coupling efficiency of BSA to tosyl functionalized beads at different temperatures, as determined using a hybridization assay, where oligonucleotide probes are bound to the BSA immobilized on the beads and then reacted with a complementary fluorescently labeled target, (see Example 6)

As shown in FIG. 4, the beads which were coupled to BSA at higher temperatures displayed more target binding to the oligonucleotide probes displayed on the bead surface. This indicates that there is a greater concentration of probes at the surface of such beads, which may be because at 65° C., BSA denatures and opens up, presenting more available binding sites to the probes.

Example 7

Figure 5:
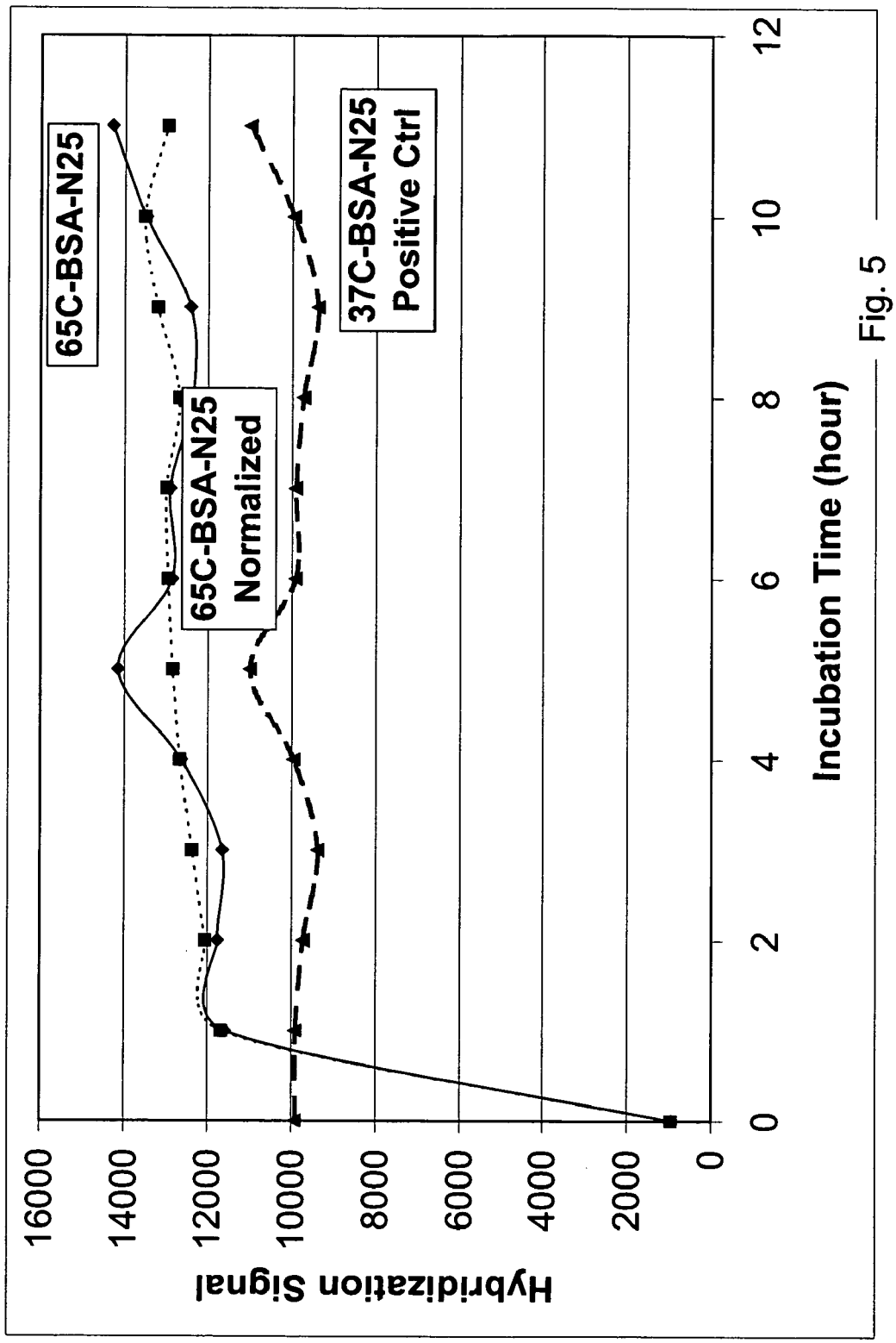
FIG. 5 indicates that for incubation at 65° C. or higher for about 1 hour, for the coupling reaction of BSA to tosyl activated beads, the binding efficiency of BSA to the bead surface is not affected, as demonstrated by the difference in hybridization signal from a target placed in contact with an oligonucleotide probe bound to BSA-coupled beads. (see Example 7)

Comparison of Varying Incubation Time for BSA Coupling to Tosyl Functionalized Particles An Experiment was conducted to study the time course of BSA coupling reaction on tosylated particles. Following the same protocol as in Examples 1 and 5 above, 12 separate tubes, each containing a BSA-tosyl particle reaction mixture, were incubated at 65° C. in an oven, and one control tube was incubated at 37° C. Each tube was taken out after a predetermined incubation period, washed and then coupled with a oligonucleotide probe (including one control probe) following method outlined in Example 3. Following this, a hybridization reaction was performed and the assay intensity was recorded (see Example 4). The results are shown in FIG. 5 which illustrates that the BSA coupling reaction is essentially complete in less than one hour.

Example 8

Comparison with Conventional Biotin-Avidin Oligonucleotide Coupling and NeutrAvidin Coating Chemistry An experiment was carried out to compare the capture and hybridization efficiency of oligo-conjugated, BSA-functionalized beads with biotinylated oligo-conjugated NeutrAvidin bead. The proteins were coupled to the bead surface at 37° C. using a protocol as outlined in Example 1. Following this, biotinylated (and also aminated) oligos were conjugated to particles (as in Example 3) and a hybridization assay was carried out with a cognate target.

Two differently encoded but otherwise identical BSA coated particles were taken and a matching probe was bound to one group and a non-matching probe was bound to the other group. Similarly two other NeutrAvidin-functionalized beads were taken and bound to matched and mismatched biotinylated probes.

Figure 6A:
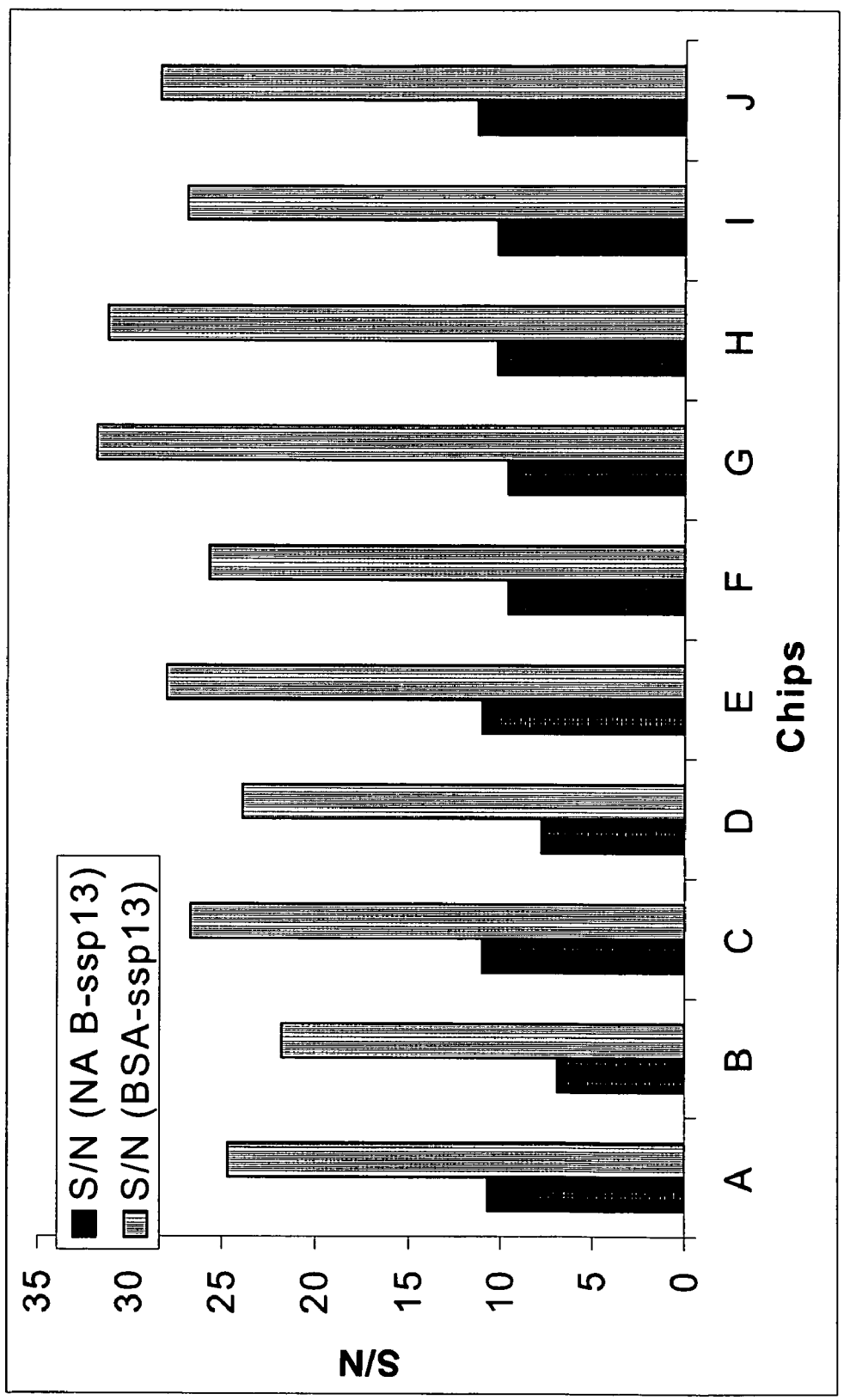
FIG. 6A shows that BSA coated tosyl functionalized beads give a more uniform and stronger hybridization signal, following bonding of probes and hybridization with a target than a Neutravidin-coated tosyl bead. (see Example 8)
Figure 6B:
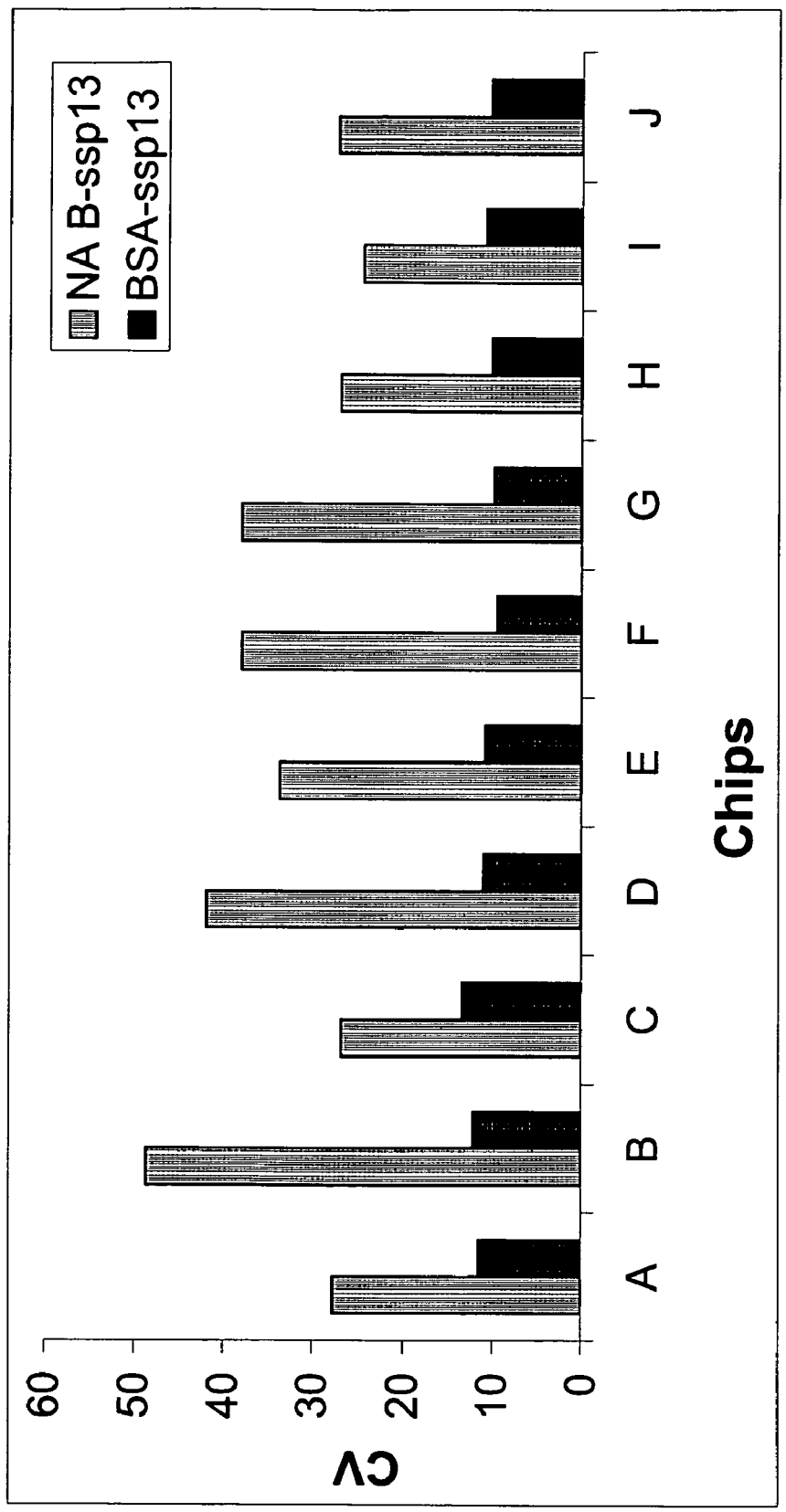
FIG. 6B shows the coefficient of variation of the signals in FIG. 6A.

The results of the assay are shown in FIGS. 6A and 6B. It is evident that BSA coating provides a more uniform (lower CV) and higher signal to noise ratio (the hybridization intensity on the mismatched probe was considered as noise) than achieved when using the NeutrAvidin capture chemistry.

Example 9

Comparison with HSA Coating

Figure 7:
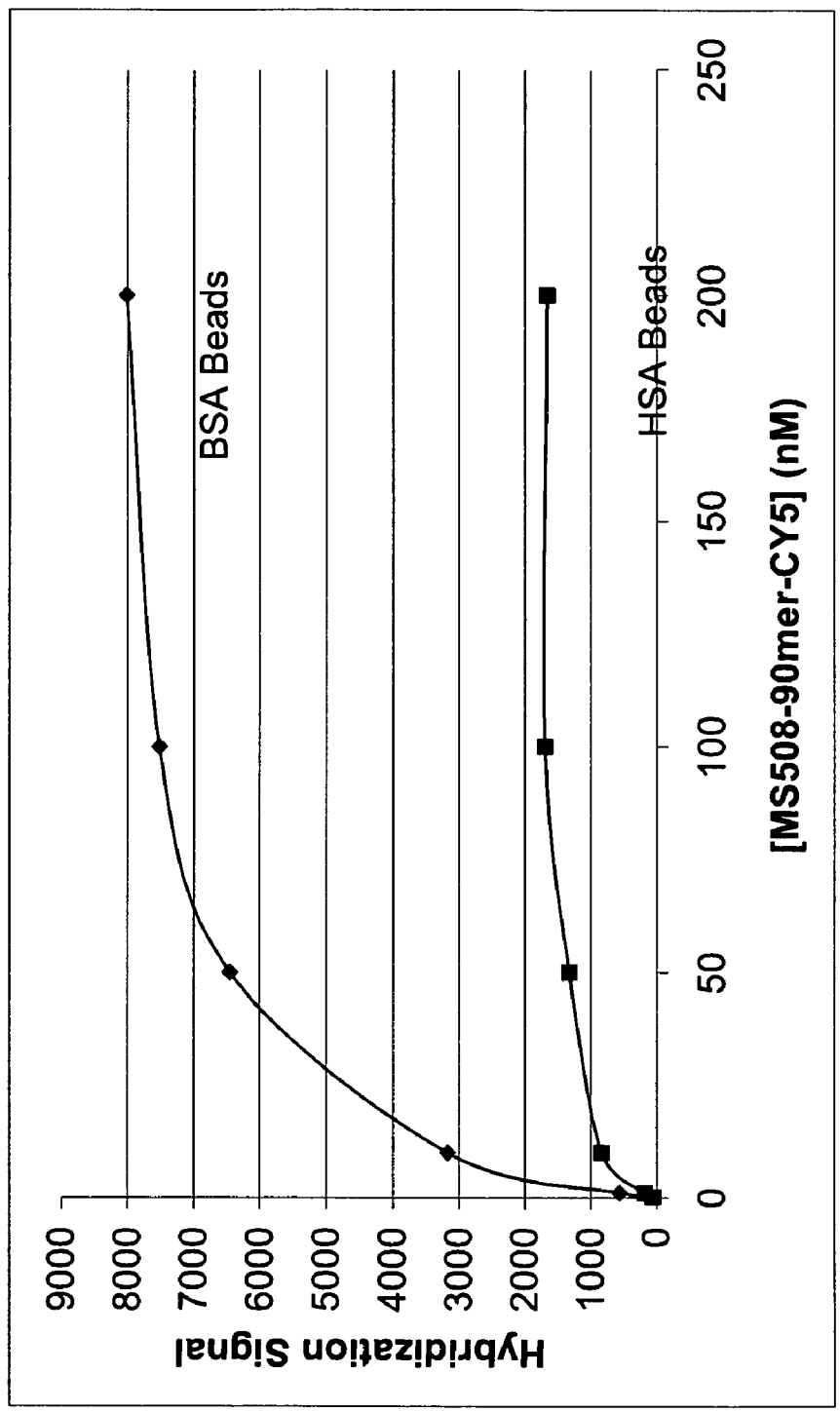
FIG. 7 shows a significant difference in hybridization when HSA, rather than BSA, is the polyelectrolyte coated on tosyl functionalized beads, where oligonucleotide probes are bound, respectively, to BSA or HSA immobilized on beads, and then reacted with a complementary fluorescently labeled target.

HSA (Human Serum Albumin) was coupled under identical conditions to those used for BSA coupling to tosyl-functionalized particles. The HSA functionalized particles were then coupled with oligonucleotide probes and hybridized (titrated) to a fluorescently labeled model DNA target (as in Example 4). The results are shown in FIG. 7. It indicates that the HSA coating is not as effective as the BSA coating for binding the oligonucleotide probes notwithstanding the fact that, like BSA, HSA has many functional carboxyl groups available for binding to the oligonucleotide probes.

Example 10

Batch to Batch Variation of BSA Coupling

Three batches of beads of 10 mg/each were separately coupled with BSA at 65° C. for 14 hours, where the BSA-bead ratio was 5 (W/W, mg/mg). The reaction volume for coupling was 3 mL. One batch of beads was coupled to BSA at 37° C. for use as a control. The coupling efficiency was determined based on signal intensity for hybridization of DNA probes coupled to the beads to cognate targets. The hybridization was done at 55° C. for 20 minutes in 1×TMAC and the target was MS508-90mer-CY5 at a concentration of 400 nM. The integration time for assay read-out is 200 ms. The results are shown in Table I.

TABLE I

| Batch | CY5 Intensity (100 ms) |
| --- | --- |
| 1 | 6864 |
| 2 | 6515 |
| 3 | 6431 |
| Control | 3964 |

The 65° C. batches had a consistently higher intensity than the batch coupled at 37° C. and also the batch to batch variability was small.

The terms, expressions and examples hereinabove are exemplary only, and not limiting, and the invention is defined only in the claims which follow and includes all equivalents of the subject matter of the claims.

What is claimed is:

1. A product comprising:
   (i) a microparticle;
   (ii) a single layer of bovine serum albumin molecules covalently attached to the microparticle;
   (iii) oligonucleotides covalently attached to the single layer wherein attachment of the single layer to the microparticle is performed at a pre-selected temperature such that the bovine serum albumin molecules in said single layer attached at said pre-selected temperature display a greater number of available sites for covalent attachment of oligonucleotides than if the single layer was attached to the microparticle at a different temperature.

2. The product of claim 1 wherein the pre-selected temperature is about 65° C.

3. The product of claim 1 wherein the oligonucleotides are bound to the protein molecules through an amide linkage, formed by an 1-ethyl-3-(3-dimethylaminopropyl) carbodiimide reaction.

4. The product of claim 1 wherein the surface of the microparticle is activated with tosyl functional group.

5. The product of claim 1 wherein the oligonucleotide is DNA, RNA, a peptide nucleic acid, a locked nucleic acid, or mixtures thereof.

6. The product of claim 1 wherein the oligonucleotide is modified at its 3' or 5' end with a functional group.

7. The product of claim 6 wherein the functional group is a primary amino group.

* * * * *